US010315982B2

(12) United States Patent
Ruppin et al.

(10) Patent No.: US 10,315,982 B2
(45) Date of Patent: Jun. 11, 2019

(54) ODOUR-MASKED AMINE COMPOSITION

(71) Applicant: Arkema France, Colombes (FR)

(72) Inventors: Christophe Ruppin, Saint-Pierre D'albigny (FR); Christian Forquy, Oloron Sainte-Marie (FR)

(73) Assignee: ARKEMA FRANCE, Colombes (FR)

( * ) Notice: Subject to any disclaimer, the term of this patent is extended or adjusted under 35 U.S.C. 154(b) by 185 days.

(21) Appl. No.: 15/116,644

(22) PCT Filed: Feb. 3, 2015

(86) PCT No.: PCT/FR2015/050239
§ 371 (c)(1),
(2) Date: Aug. 4, 2016

(87) PCT Pub. No.: WO2015/118254
PCT Pub. Date: Aug. 13, 2015

(65) Prior Publication Data
US 2016/0340292 A1    Nov. 24, 2016

(30) Foreign Application Priority Data
Feb. 6, 2014  (FR) .................................. 14 50914

(51) Int. Cl.
*C07C 209/90* (2006.01)
*C08K 5/01* (2006.01)
*C08K 5/06* (2006.01)
*C08K 5/1525* (2006.01)
*C08K 5/17* (2006.01)
*C08K 5/29* (2006.01)

(52) U.S. Cl.
CPC .............. *C07C 209/90* (2013.01); *C08K 5/01* (2013.01); *C08K 5/06* (2013.01); *C08K 5/1525* (2013.01); *C08K 5/17* (2013.01); *C08K 5/29* (2013.01)

(58) Field of Classification Search
CPC .................................................. C07C 209/90
See application file for complete search history.

(56) References Cited

U.S. PATENT DOCUMENTS

| 4,840,792 A | 6/1989 | Joulain | |
|---|---|---|---|
| 5,382,691 A * | 1/1995 | Stern | C07C 209/00 564/415 |
| 2003/0068295 A1* | 4/2003 | Rohde | A61L 9/01 424/76.1 |
| 2004/0166087 A1* | 8/2004 | Gembala | A61L 9/01 424/76.1 |
| 2006/0281951 A1* | 12/2006 | Lee | C07C 209/84 564/511 |
| 2010/0126690 A1* | 5/2010 | Van Hemelryck | B22C 1/162 164/525 |
| 2011/0166387 A1* | 7/2011 | Ruppin | C07C 209/26 564/471 |

FOREIGN PATENT DOCUMENTS

| EP | 0141266 | 5/1985 |
|---|---|---|
| EP | 0247946 | 12/1987 |
| EP | 1955792 | 8/2008 |
| JP | 08302383 | 11/1996 |
| WO | 2005110499 | 11/2005 |
| WO | 2006138132 | 12/2006 |
| WO | 2012121359 | 9/2012 |

OTHER PUBLICATIONS

Hexylamine Certificate of Analysis, Acros Organics Aug. 14, 2012.*
Peppermint Oil Safety Data Sheet, Bontoux, Inc. Aug. 4, 2014 (Year: 2014).*
International Search Report and Written Opinion for International Aplication PCT/FR2015/050239, dated Apr. 21, 2015, 9 pages.

* cited by examiner

*Primary Examiner* — Michael F Pepitone
(74) *Attorney, Agent, or Firm* — RatnerPrestia

(57) ABSTRACT

The present invention relates to a composition comprising: a) at least one primary, secondary or tertiary amine and b) at least one agent which masks the odor of said at least one amine, said at least one odor-masking agent comprising at least one ether (b1), optionally, but preferably, at least one terpene and/or one terpenoid (b2) and optionally, but preferably, at least one oxime (b3). The invention also relates to the use of an odor-masking agent in order to mask the odor of at least one amine.

23 Claims, No Drawings

ODOUR-MASKED AMINE COMPOSITION

CROSS-REFERENCE TO RELATED APPLICATIONS

This is the national phase of International Application No. PCT/FR2015/050239, filed 3 Feb. 2015, which claims priority from French Application No. 1450914, filed 6 Feb. 2014. The entire disclosure of each of these applications is incorporated herein by reference in its entirety for all purposes.

FIELD OF THE INVENTION

The present invention relates to an odor-masked amine composition, to the process for the preparation thereof, and also to uses of said odor-masked amine composition.

BACKGROUND OF THE RELATED ART

Amines are organic compounds currently very widely used in numerous sectors of industry, for example as catalysts or crosslinking agents in the field of polymer synthesis, and in particular polyurethane synthesis, or else as additives in lubricants, paints, and others.

One drawback of organic amines may in some cases arise from their odor, which is more or less strong, more or less pronounced, and more or less nauseating. Some amines even give off such strong and/or unpleasant odors that they must be handled in a closed chamber, or else even with breathing equipment intended for the technical personnel, which is accompanied by logistical problems and associated costs.

Thus, for example, amines, more particularly tertiary amines or mixtures of tertiary amines, are currently used in the manufacture of polymers, for example polyurethanes, for manufacturing car seats, for manufacturing cores for foundry molds, and others, to name but a few of the possible fields of applications.

More specifically, the manufacture of cores for foundry molds makes use of a process referred to as the "Ashland process" (or else the "cold box process"), in which process a binder comprising a polyol resin and an isocyanate is added to a mass of sand to be hardened. A polymerization agent is then injected in aerosol form into the mass of sand to be hardened containing the binder, causing instantaneous curing of the resin. The curing is obtained by a polyaddition reaction between the polyol resin and the isocyanate in the presence of the polymerization agent.

In this process, the polymerization agent used consists of amine(s) or a mixture of amines, and more particularly tertiary amines, which most often have strong, nauseating odors. When the amines are injected and curing is obtained, the excess amines are eliminated by a flow of rinsing air, before being treated. Inevitably, residual traces of amines are present and generate bad, bothersome odors which are just as damaging to the workers of the industrial sites.

In order to eliminate the release of malodorous compounds into the atmosphere, chemical scrubbing towers are generally used in foundries. These scrubbing towers make use of absorption techniques able to convert the malodorous molecules from the gas phase to the liquid phase by means of exchange columns. However, this treatment does not make it possible to eliminate, or at the very least effectively reduce, the unpleasant odor that these amines generate upstream, that is to say before the use thereof by the workers in the factories.

Patent application JP8302383 proposes a perfuming composition comprising at least one aldehyde, having a $C_6$-$C_{15}$ carbon-based chain, and at least one ester. This composition makes it possible to mask the bothersome odor of tertiary amines, and especially the tertiary amines used as polymerization agent in the production of polyurethane, by spraying this odorizing composition into the air of the chambers polluted by the odors of said amines.

International application WO2012/121359 proposes a deodorizing composition comprising at least one dicarboxylic acid and at least one tricarboxylic acid as active agents, and metal acid salts. This deodorizing composition is described as making it possible to eliminate amine odors. Indeed, the carboxylic acids and the metal acid salts are used to neutralize the amine residues which are thus salified.

Thus, none of the solutions currently known is able to overcome the abovementioned drawbacks, and there remains a real need to eliminate, or at least effectively reduce, the unpleasant odors that the amines, and in particular the tertiary amines, generate, by economical and simple means.

BRIEF SUMMARY OF THE INVENTION

The inventors have now discovered that it is possible to odorize amines, in order to mask, entirely or at least very substantially, the odors thereof which are nauseating and troublesome for users and the environment.

Thus, a first subject of the present invention is a composition comprising:

a) at least 90% by weight, more preferentially still at least 95%, advantageously at least 99%, more advantageously still at least 99.5% by weight of at least one primary, secondary or tertiary amine, relative to the total weight of the composition, and b) at most 10%, more preferentially still at most 5%, advantageously at most 1%, more advantageously still at most 0.5%, particularly preferably at most 0.25%, more preferably still at most 0.2%, particularly preferably at most 0.1%, more preferably still at most 0.08% by weight of an odor-masking agent (b), relative to the total weight of the composition.

According to one embodiment, said at least one amine present in the composition according to the present invention is an amine of formula (I):

in which:

$R_1$, $R_2$ and $R_3$, which may be identical or different, are selected independently of one another from a hydrogen atom, a linear or branched alkyl radical comprising from 1 to 12 carbon atoms and a cycloalkyl radical comprising from 3 to 12 carbon atoms, two of the substituents selected from $R_1$, $R_2$ and $R_3$ optionally, together and with the nitrogen atom to which they are bonded, forming a ring structure comprising from 2 to 12 carbon atoms, and optionally comprising one or more heteroatoms selected from oxygen, nitrogen, sulfur and phosphorus, and being optionally substituted with one or more functional groups selected from hydroxyl, alkoxy, alkylcarbonyl, alkoxycarbonyl, benzyl, fluorine, chlorine, bromine, iodine, sulfur, phosphorus and nitrogen.

According to one embodiment, said odor-masking agent comprises:

at least one ether of formula (b1):

$$R_4\text{—}O\text{—}R_5 \qquad (b1)$$

in which:
- $R_4$ and $R_5$, which may be identical or different, are selected independently of one another from a linear or branched alkyl radical comprising from 1 to 12 carbon atoms, a cycloalkyl radical comprising from 3 to 12 carbon atoms, an alkenyl radical comprising from 2 to 12 carbon atoms, a cycloalkenyl radical comprising from 3 to 12 carbon atoms, a phenyl radical and a benzyl radical,
- $R_4$ and $R_5$ optionally, together and with the oxygen atom to which they are bonded, forming a ring structure comprising from 3 to 20 atoms, and optionally comprising one or more heteroatoms selected from oxygen, nitrogen, sulfur and phosphorus, said ring structure being optionally substituted with one or more groups selected from hydroxyl, alkoxy, alkylcarbonyl, alkoxycarbonyl, phenyl, benzyl, fluorine, chlorine, bromine, iodine, sulfur, phosphorus and nitrogen, optionally but preferably at least one terpene and/or one terpenoid (b2) and optionally but preferably at least one oxime of formula (b3):

in which:
- $R_6$ is selected from a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, the phenyl radical and the benzyl radical, and $R_7$ is selected from a hydrogen atom, and a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, the phenyl radical and the benzyl radical,
- $R_6$ and $R_7$ optionally, together and with the carbon atom to which they are bonded, forming a ring structure comprising from 3 to 20 atoms, and optionally comprising one or more heteroatoms selected from oxygen, nitrogen, sulfur and phosphorus, said ring structure being optionally substituted with one or more groups selected from hydroxyl, alkoxy, phenyl, benzyl, fluorine, chlorine, bromine, iodine, sulfur, phosphorus and nitrogen.

A subject of the present invention is a composition comprising:
a) at least 90% by weight, more preferentially still at least 95%, advantageously at least 99%, more advantageously still at least 99.5% by weight of at least one primary, secondary or tertiary amine, relative to the total weight of the composition, and b) at most 10%, more preferentially still at most 5%, advantageously at most 1%, more advantageously still at most 0.5%, particularly preferably at most 0.25%, more preferably still at most 0.2%, particularly preferably at most 0.1%, more preferably still at most 0.08% by weight of an odor-masking agent (b), relative to the total weight of the composition;

in which said odor-masking agent comprises:
at least one ether of formula (b1):

$$R_4\text{—}O\text{—}R_5 \qquad (b1)$$

in which:
- $R_4$ and $R_5$, which may be identical or different, are selected independently of one another from a linear or branched alkyl radical comprising from 1 to 12 carbon atoms, a cycloalkyl radical comprising from 3 to 12 carbon atoms, an alkenyl radical comprising from 2 to 12 carbon atoms, a cycloalkenyl radical comprising from 3 to 12 carbon atoms, a phenyl radical and a benzyl radical,
- $R_4$ and $R_5$ optionally, together and with the oxygen atom to which they are bonded, forming a ring structure comprising from 3 to 20 atoms, and optionally comprising one or more heteroatoms selected from oxygen, nitrogen, sulfur and phosphorus, said ring structure being optionally substituted with one or more groups selected from hydroxyl, alkoxy, alkylcarbonyl, alkoxycarbonyl, phenyl, benzyl, fluorine, chlorine, bromine, iodine, sulfur, phosphorus and nitrogen, optionally but preferably at least one terpene and/or one terpenoid (b2) and optionally but preferably at least one oxime of formula (b3):

in which:
- $R_6$ is selected from a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, the phenyl radical and the benzyl radical, and $R_7$ is selected from a hydrogen atom, and a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, the phenyl radical and the benzyl radical, $R_6$ and $R_7$ optionally, together and with the carbon atom to which they are bonded, forming a ring structure comprising from 3 to 20 atoms, and optionally comprising one or more heteroatoms selected from oxygen, nitrogen, sulfur and phosphorus, said ring structure being optionally substituted with one or more groups selected from hydroxyl, alkoxy, phenyl, benzyl, fluorine, chlorine, bromine, iodine, sulfur, phosphorus and nitrogen.

According to another embodiment, said odor-masking agent comprises:
a) at least 90% by weight, more preferentially still at least 95%, advantageously at least 99%, more advantageously still at least 99.5% by weight of at least one primary, secondary or tertiary amine, relative to the total weight of the composition, and b) at most 10%, more preferentially still at most 5%, advantageously at most 1%, more advantageously still at most 0.5%, particularly preferably at most 0.25%, more preferably still at most 0.2%, particularly preferably at most 0.1%, more preferably still at most 0.08% by weight of an odor-masking agent (b), relative to the total weight of the composition;

in which said odor-masking agent comprises:
  at least one ether of formula (b1), as defined above,
  at least one terpene and/or one terpenoid (b2) and
  optionally but preferably at least one oxime of formula (b3) as defined above.

According to yet another embodiment, said odor-masking agent comprises:

a) at least 90% by weight, more preferentially still at least 95%, advantageously at least 99%, more advantageously still at least 99.5% by weight of at least one primary, secondary or tertiary amine, relative to the total weight of the composition, and b) at most 10%, more preferentially still at most 5%, advantageously at most 1%, more advantageously still at most 0.5%, particularly preferably at most 0.25%, more preferably still at most 0.2%, particularly preferably at most 0.1%, more preferably still at most 0.08% by weight of an odor-masking agent (b), relative to the total weight of the composition;

in which said odor-masking agent comprises:
  at least one ether of formula (b1), as defined above,
  at least one terpene and/or one terpenoid (b2) and
  at least one oxime of formula (b3), as defined above.

In the description of the present invention, unless specifically indicated otherwise, the alkyl, cycloalkyl, alkenyl, and cycloalkenyl radicals may optionally be substituted by one or more groups selected from hydroxy, alkoxy, alkylcarbonyl, alkoxycarbonyl, phenyl, benzyl, fluorine, chlorine, bromine, iodine, sulfur, phosphorus and nitrogen, and preferably selected from hydroxy, alkoxy, phenyl, benzyl, fluorine, chlorine, bromine, phosphorus and nitrogen.

In addition, alkyl and alkoxy radicals comprising from 1 to 6 carbon atoms, more preferably still from 1 to 4 carbon atoms, are preferred.

According to one preferred embodiment, at least one of the radicals $R_1$, $R_2$ and $R_3$ does not represent a hydrogen atom, since the invention does not aim to odorize ammonia but does aim to odorize primary, secondary or tertiary amines.

According to another preferred embodiment of the invention, at least two of the radicals $R_1$, $R_2$ and $R_3$ do not represent a hydrogen atom, since the invention aims to odorize secondary or tertiary amines.

According to yet another preferred embodiment of the invention, none of the radicals $R_1$, $R_2$ and $R_3$ represents a hydrogen atom, since the invention aims to odorize tertiary amines.

According to one preferred embodiment, the invention relates to a composition comprising at least one amine of formula (I) as defined previously and an odor-masking agent as defined previously in the proportions indicated above.

DETAILED DESCRIPTION OF CERTAIN EMBODIMENTS OF THE INVENTION

Thus, the present invention offers a simple, effective and economical means which makes it possible to mask the odors of amines, preferably primary, secondary or tertiary amines, preferably secondary or tertiary amines, more preferably still tertiary amines, but also alkylalkanolamines (referred to by the acronym "AAA") and also amines comprising two, three or four nitrogen atoms (referred to by the name "polyamines").

As examples of primary amines which may be used in the present invention, mention may be made, non-limitingly, of: propan-1-amine, propan-2-amine, cyclopentanamine, 2-methylpropan-2-amine, phenylmethanamine, 2-aminopentane, 3-aminopentane, 1,2-dimethylpropylamine, hexylamine, 1,3-dimethylbutylamine, n-heptylamine, n-octylamine, 2-aminooctane, 3,3,5-trimethylcyclohexylamine, ethylamine (MEA), isopropylamine, sec-butylamine, 3-ethoxypropylamine, 3-(2-methoxyethoxy)propylamine, 3-butoxypropylamine, 3-(2-ethylhexyloxy)propylamine, 3-isopropoxypropylamine and 3-methoxypropylamine, and also mixtures of two or more thereof in any proportions.

As examples of secondary amines which may be used in the present invention, mention may be made, non-limitingly, of: N-methylethanamine, N-ethylethanamine, N-methylpentan-3-amine, N-3-dimethylbutan-2-amine, di(sec-butyl)amine, diamylamine, isopropylbenzylamine, dihexylamine, diethylamine, diisopropylamine, N-isopropylmethylamine, N-butylmethylamine, N-(sec-butyl)methylamine, N-isobutylmethylamine, N-(tert-butyl)methylamine, N-methylpentylamine, N-hexylmethylamine, N-methylcyclohexylamine, N-heptylmethylamine, N-octylmethylamine, N-ethylmethylamine, N ethylpropylamine, N-ethylisopropylamine, N-butylethylamine, N-(sec-butyl)ethylamine, N-ethylcyclohexylamine and N-ethylbenzylamine, and also mixtures of two or more thereof in any proportions.

As examples of tertiary amines which may be used in the present invention, mention may be made, non-limitingly, of: trimethylamine, N-methylaziridine, dimethylethylamine (DMEA), N-methylazetidine, N-ethylaziridine, diethylmethylamine (DEMA), dimethylisopropylamine (DMIPA), dimethyl(n-propyl)amine (DMPA), N-(n-propyl)aziridine, N-isopropylaziridine, N-ethylazetidine, N-methylpyrrolidine, N,N,N',N'-tetramethyldiaminomethane, triethylamine (TEA), methylethyl(n-propyl)amine, methylethylisopropylamine, dimethyl(n-butyl)amine, dimethyl(sec-butyl)amine, dimethylisobutylamine, dimethyl(tert-butyl)amine, N-ethylpyrrolidine, N-methylpiperidine, hexamethylenetetramine, dimethylpiperazine, N,N,N',N'-tetramethyldiaminoethane, dimethylpentylamines, methylethylbutylamines, diethylamines, dipropylmethylamines, N-propylpyrrolidines, N-ethylpiperidine, dimethylhexylamines, methylethylpentylamines, diethylbutylamines, dipropylethylamines, N-butylpyrrolidines, N-propylpiperidines, diethylpiperazine, dimethylheptylamines, methylethylhexylamines, diethylpentylamines, tripropylamines, N-pentylpyrrolidines, N-butylpiperidines, dimethyloctylamines, methylethylheptylamines, diethylhexylamines, ethylpropylpentylamines, dipropylbutylamines, N-pentylpiperidines and ethyldiisopropylamine, and also mixtures of two or more thereof in any proportions.

As examples of alkylalkanolamines of formula (I) which may be used in the present invention, mention may be made, non-limitingly, of: aminopropyldiethanolamine, 2,2'-(heptylamino)bisethanol, alaninol, 2-(ethylamino)ethanol, 2-isopropylaminoethanol, 2-butylaminoethanol, 2-benzylaminoethanol, 2-(3-aminopropylamino)ethanol, 2-octylaminoethanol, 2-sec-butylaminoethanol, N-butyldiethanolamine, N-sec-butyldiethanolamine, 2-(dibutylamino)ethanol, N-benzyl-N-methylethanolamine, N-heptyldiethanolamine, N-octyldiethanolamine, and also mixtures of two or more thereof in any proportions.

As examples of polyamines which may be used in the present invention, mention may be made, non-limitingly, of: tetramethylpropylenediamine (TMPDA), diethylaminopropylamine (DEAPA), dimethylaminopropylaminopropylamine (DMAPAPA), N-methyl-1,3-diaminopropane, N-propyl-1,3-propanediamine, N-isopropyl-1,3-propanediamine, N,N,N'-trimethyl-1,3-propanediamine, 1-(3-aminopropyl)-2-pyrrolidine, 3-morpholinopropylamine, 1-(3-aminopropyl)piperidine, 1-(3-aminopropyl)-2-pipecoline, N-cyclohexyl-1,3-propanediamine, 3-(dibutylamino)propylamine, 2-(3-aminopropylamino)ethanol, N-(aminopropyl)diethanolamine (APDEA), 3-(2-aminoethyl)aminopropylamine, bis(3-aminopropyl)amine, methyl-bis-(3-aminopropyl)amine, N-(3-aminopropyl)-1,4-diaminobutane, pentamethyldipropylenetriamine, 1,2-bis(3-aminopropylamino)ethane, N,N'-bis(3-aminopropyl)-1,3-propanediamine, 1,4-bis-(3-aminopropyl)piperazine, and also mixtures of two or more thereof in any proportions.

The most particularly preferred amines used in the compositions of the present invention are tertiary amines selected from DMEA, DMIPA, DEMA, DMPA and TEA, and also mixtures of two or more thereof in any proportions. DMEA, and also mixtures of DMEA with one or more other amines of formula (I), are most particularly preferred.

According to the present invention, it is now possible to mask the odor of primary, secondary and/or tertiary amines, in particular amines of formula (I), and also mixtures of two or more thereof in any proportions, as they have just been defined. Preferably, the odor-masking agent must not react with the amine to be odorized and is generally selected from odor-masking agents bearing functions which do not chemically react with amine functions, especially under storage conditions. Thus, odor-masking agents are preferred that do not have compounds bearing acid, ester, aldehyde and other functions. Such odor-masking agents may nonetheless be used, however in proportions not exceeding 0.5% by weight, limit value excluded, preferably 0.4% by weight and even more preferentially still not exceeding 0.2% by weight relative to the total weight of odor-masking agents. In addition, compositions are preferred that are stable over time, having a minimum shelf life of greater than 1 month, preferably greater than 3 months, preferentially greater than 6 months, and even more preferentially greater than 12 months. As will be indicated below, the odor of the amine(s) is masked effectively by means of an odor-masking agent comprising at least one ether of formula (b1), optionally but preferably at least one terpene and/or one terpenoid (b2) and optionally but preferably at least one oxime (b3).

As examples of ethers (b1) which may be used as constituent of the odor-masking agent, mention may be made, non-limitingly, of: phenoxybenzene, diphenyl ether, methoxynaphthalenes, 1-methoxy-4-methyl-(4-methylanisole), 2-(2,4-dimethylcyclohex-3-en-1-yl)-5-methyl-(1-methylpropyl)-1,3-dioxane, methoxymethane, methoxyethane, ethoxyethane, 2-ethoxypropane, oxacyclopropane, oxacyclopentane, oxacyclohexane, 1,4-dioxacyclohexane, dimethoxymethane, diisopropyl ether, tetrahydrofuran, 1,4-dioxane, pyrans, dihydropyrans, phenylpyrans, dihydrophenylpyrans, and pyrans and dihydropyrans substituted by a phenyl and an alkyl (for example methyl, ethyl, propyl or butyl) and others, and also mixtures of two or more thereof in any proportions.

As examples of terpenes and terpenoids (b2) which may be used as constituent of the odor-masking agent, mention may be made, non-limitingly, of: terpinenes, myrcene, limonene, terpinolene, pinenes, sabinene, camphene, ocimene, eucalyptol, citral, menthol, camphor, menthone, terpineol, isoborneol, nerol, citronellal, citronellol, linalool, geraniol and myrcenol, and also mixtures of two or more thereof in any proportions, and also essential oils based on terpenes and/or terpenoids, especially those comprising these constituents.

The odor-masking agent (b) may also comprise one or more oximes (b3), and most particularly an aldoxime or a ketoxime, preferably a ketoxime. Among the oximes (b3), mention may be made, as non-limiting examples, of the oximes for which $R_7$ represents a hydrogen atom or a radical selected from methyl, ethyl, n-propyl, isopropyl, n-butyl, sec-butyl and tert-butyl, and $R_6$ is selected from linear or branched alkyl radicals comprising from 1 to 12 carbon atoms, preferably from 1 to 8 carbon atoms, more preferably still from methyl, ethyl, n-propyl, isopropyl, n-butyl, sec-butyl, tert-butyl, n-pentyl, isopentyl, tert-pentyl, neopentyl, and linear or branched hexyl radicals.

According to one preferred aspect, non-limiting examples of oximes (b3) comprise cinnamaldehyde oxime, 2-methylbutanal oxime, 3-methylbutanal oxime, methyl ethyl ketoxime, 3-heptanone oxime, 5-methyl-3-heptanone oxime, glyoxime, dimethylglyoxime, diaminoglyoxime, pralidoxime, obidoxime, perillartine, asoxime chloride and salicylaldoxime, and also mixtures of two or more thereof in any proportions.

When reference is made to ranges, expressions of the type "extending from . . . to . . . " include the limit values of the range. Conversely, expressions of the type "between . . . and . . . " exclude the limit values of the range. When reference is made to value thresholds, the expressions "at most" or "at least" respectively exclude the maximum value and the minimum value. Unless indicated otherwise, the percentages are given as weight values.

The respective amounts of each of the constituents (b1), (b2) and (b3) of the odor-masking agent (b) may vary within broad proportions according to the nature of the constituents (b1), (b2) and (b3) and according to the nature of the amine or amines whose odor it is desired to mask.

According to one preferred embodiment, the composition according to the invention comprises, as % by weight relative to the total weight of the odor-masking agent:

from 1% to 100%, preferably from 2% to 100%, preferably from 5% to 100%, more preferably still from 10% to 100%, of at least one ether (b1), from 0% to 99%, preferably from 1% to 99%, preferably from 2% to 99%, preferably from 5% to 99%, more preferably still from 10% to 99%, of at least one terpene and/or terpenoid (b2), from 0 to 50%, preferably from 0 to 20%, advantageously from 0 to 10%, of at least one oxime (b3), and optionally one or more additives, q.s for 100%.

According to one more preferred embodiment, the composition according to the invention comprises, as % by weight relative to the total weight of the odor-masking agent:

from 1% to 99%, preferably from 2% to 99%, preferably from 5% to 99%, more preferably still from 10% to 99%, of at least one ether (b1), from 1% to 99%, preferably from 2% to 99%, preferably from 5% to 99%, more preferably still from 10% to 99%, of at least one terpene and/or terpenoid (b2), from 0% to 10%, preferably from 0% to 5%, preferably from 0% to 2%, more preferably still from 0% to 1%, of at least one oxime (b3), and optionally one or more additives, q.s for 100%.

According to one particularly preferred embodiment, the composition according to the invention comprises, as % by weight relative to the total weight of the odor-masking agent:

from 1% to 98.9%, preferably from 2% to 98.9%, preferably from 5% to 98.9%, more preferably still from 10% to 98.9%, of at least one ether (b1), from 1% to 98.9%, preferably from 2% to 98.9%, preferably from 5% to 98.9%, more preferably still from 10% to 98.9%, of at least one terpene and/or terpenoid (b2), from 0.1% to 10%, preferably from 0.1% to 5%, preferably from 0.1% to 2%, more preferably still from 0.1% to 1%, of at least one oxime (b3), and optionally one or more additives, q.s for 100%.

According to another particularly preferred embodiment, the composition according to the invention comprises, as % by weight relative to the total weight of the odor-masking agent:

from 1% to 98%, preferably from 2% to 98%, preferably from 5% to 98%, more preferably still from 10% to 98%, of at least one ether (b1), from 1% to 98%, preferably from 2% to 98%, preferably from 5% to 98%, more preferably still from 10% to 98%, of at least one terpene and/or terpenoid (b2), from 1% to 10%, preferably from 1% to 5%, more preferably still from 1% to 2%, of at least one oxime (b3), and optionally one or more additives, q.s for 100%.

Among the odor-masking agents (b), preference is in addition given to those comprising at least two different ethers, more preferably still those comprising at least three different ethers.

The additives which may be present in the masking agents (b) may be of all types known to those skilled in the art, and advantageously those known to those skilled in the art and compatible with the envisaged application.

Non-limiting examples of additives which may be used in the odor-masking agents (b) comprise solvents, pigments, dyes, preserving agents, antioxidants, fragrances and others.

The additives optionally present in the odor-masking agent may comprise one or more chemical functions selected from aldehyde, ketone, ester and alcohol. According to one preferred embodiment, the additives are selected from those comprising one or more ester functions. Additives comprising at least one alcohol function are not preferred.

Among the additives of aldehyde or ketone type, mention may be made, nonlimitingly, of geranial, neral, citronellal, damascones, damascenones, ionones, irisones, methylionones, frambinone, dynascone, menthone, isomenthone, flavonone and mixtures thereof.

Among the additives of ester type, mention may be made, non-limitingly, of saturated or unsaturated $C_2$-$C_{20}$ acid esters, such as ethyl, propyl, butyl, pentyl, 2-methylbutyl, isoamyl, hexyl, benzyl, phenylethyl, menthyl or carvyl acetates, propionates, butyrates, methylbutyrates, pentanoates, hexanoates, heptanoates, caproates, oleates, linoleates or linolenates, but also ortho-phthalates, such as diethyl ortho-phthalate, citrates, such as triethyl citrate, malonates, such as diethyl malonate, and others, and also the mixtures of two or more thereof in any proportions.

Among the additives of alcohol type, mention may be made, non-limitingly, of monoalcohols comprising from 1 to 30 carbon atoms, preferably from 6 to 20 carbon atoms, more preferably still from 8 to 11 carbon atoms, said carbon atoms forming a linear or branched chain optionally comprising one or more unsaturation(s) in the form of double bond(s), and optionally comprising a saturated or completely or partially unsaturated 5- or 6-membered ring structure selected from menthol, neomenthol, phenylethyl alcohol, benzyl alcohol, citronellol, dihydromyrcenol, dihydroterpineol, linalool, ethyllinalool, tetrahydrolinalool, tetrahydromyrcenol, geraniol, nerol, and others, and also the mixtures of two or more thereof in any proportions.

The odor-masking agent (b) thus defined affords the advantage of particularly effectively masking the unpleasant odor of amines, and particularly tertiary amines, without modifying the chemical structure thereof. In addition, and as indicated previously, the odor-masking agent must not react with the amine to be odorized and must also be stable over time in the composition in which it is incorporated according to the invention.

Another subject of the present invention is a process for preparing said odor-masked amine composition comprising a step of mixing at least one amine, preferably an amine of formula (I), with at least one odor-masking agent (b).

The mixing may be carried out by any method known to those skilled in the art, and especially by introducing at least one odor-masking agent (b), optionally but advantageously in liquid form, at room temperature or with heating, with or without stirring, into at least one amine of formula (I), by any means known to those skilled in the art, such as, for example and non-limitingly, by metering pump, dip pipe into a storage tank, spraying, and others.

The composition according to the invention may for example be prepared under atmospheric pressure, at a temperature of between 0° C. and 100° C., preferably of between room temperature and approximately 80° C. Preparation may also be carried out under pressure or negative pressure, at temperatures within the ranges indicated above.

The composition according to the invention may be in liquid or gas form and in a predetermined concentration range as seen above, alone or in combination with an inert gas. The inert gas may be nitrogen, air or carbon dioxide. Preferably, the composition according to the invention is in liquid form at room temperature and ambient pressure.

According to one embodiment, the composition according to the present invention comprising at least one amine of formula (I) and at least one odor-masking agent (b), as defined previously, may be diluted by one or more solvents before use. The dilution solvents which may be used may be of any type known to those skilled in the art, and comprise for example solvents and mixtures of aqueous, organic or aqueous-organic solvents. Moreover, solvents which are compatible with the envisaged application are preferred. In a particularly preferred embodiment, the solvent is selected from water, ethanol, n-propanol, isopropanol, n-butanol, isobutanol and mixtures of two or more thereof in any proportions. According to a most particularly preferred aspect, the composition according to the invention is diluted in water, and in a particularly advantageous embodiment the dilution water is the water present in the amine(s) of formula (I), for example the water present, or formed, during synthesis of the amine(s) of formula (I).

It has been discovered, surprisingly, that the addition of at least one odor-masking agent (b) into at least one amine of formula (I) makes it possible to entirely satisfactorily reduce, or even to eliminate, bothersome or nauseating odors from said at least one amine.

Thus, and according to another subject, the present invention relates to the use of at least one odor-masking agent (b) comprising at least one ether, optionally but preferably at least one terpene and/or one terpenoid and optionally but preferably at least one oxime, to mask the odor of at least one amine, preferably at least one amine of formula (I), preferably at least one secondary or tertiary amine of formula (I), more preferably still at least one tertiary amine of formula (I), which formula (I) is as defined previously.

According to one preferred embodiment of this subject, the present invention relates to the use of at least one odor-masking agent (b) as defined previously, to mask the odor of a mixture of at least two amines, preferably of at least two tertiary amines of formula (I) as defined previously.

The composition comprising at least one amine of formula (I) and at least one odor-masking agent (b) as they have just been defined according to the invention may be used for numerous applications, and generally may be used like any amine composition(s) not comprising an odor-masking agent. Indeed, and as another advantage, the composition of the present invention is stable, and the amine(s) included in this composition do not undergo degradation, such as loss of properties, yellowing and others.

The composition according to the present invention may thus be used like any other amine or amine mixture not comprising an odor-masking agent, the composition of the invention having an improved odor relative to the same amine(s) not comprising an odor-masking agent (b).

As non-limiting examples of possible applications for the composition according to the present invention, mention may be made of those in which amines are used as synthesis intermediates in fine chemistry, and in particular of pharmaceutical products and products for agrochemistry, such as acid scavengers during syntheses of chemical products, as catalysts and crosslinking agents for the preparation of polymers, as additives for lubricants and for paints, and others.

As a most particularly preferred example of the use of the composition according to the present invention, mention may be made of the manufacture of polymers, for example of polyurethanes, especially for the manufacture of car seats, or most particularly for the manufacture of foundry molds, especially of cores for foundry molds, for example according to the "Ashland" process described in document EP-A-1 955 792.

Indeed, during the use of the composition according to the invention in the foundry field, it has been discovered that said composition used as polymerization agent was compatible with the compounds and the conditions employed in said "Ashland" process or the process referred to as "cold box process". The odor-masking agent makes it possible to particularly effectively mask the unpleasant odor of the amines used, without reacting with the various compounds required for the formation of a foundry mold.

In particular, the composition according to the present invention may be used under the same reaction conditions as amines, and especially tertiary amines used as described in document EP-A-1 955 792, that is to say in vaporized form and typically in vaporized form in a mixture with an inert gas.

Thus, and according to another subject, the present invention relates to a process for manufacturing foundry molds comprising at least the following steps:
 a) preparing a mixture comprising a binder and an aggregate, said aggregate preferably being sand,
 b) shaping, in a mold, of the mixture obtained in step a),
 c) placing the shaped mixture in contact with at least one composition according to the present invention, in liquid or gas form, preferably in gas form, and optionally with an inert vector,
 d) crosslinking of the binder/aggregate mixture to give a foundry mold of hard, solid and crosslinked form, and
 e) recovering the foundry mold.

The term "foundry mold" also denotes foundry cores, in other words those pieces of the mold which make it possible to produce internal recesses in a molded piece or in undercut zones thereof.

The inert vector optionally used in step c) is advantageously an inert gas or a mixture of inert gases, for example nitrogen and/or carbon dioxide.

In the process for preparing a foundry mold described above, the composition of the invention comprises at least one, preferably tertiary, amine, most particularly preferably a mixture of at least two amines, at least one of which, or even at least two of which, are tertiary amines, at least one masking agent (b) and optionally water, and when water is present, the content thereof preferably does not exceed 1%, more preferably still does not exceed 0.5% by weight relative to the total weight (water, amine(s) and odor-masking agent(s)).

According to yet another aspect, the present invention relates to a foundry mold substantially obtained according to the process described above, and more particularly relates to a foundry mold obtained by crosslinking a binder mixed with an aggregate by means of a composition according to the invention comprising at least one amine of formula (I) as defined previously and at least one odor-masking agent (b) as defined previously.

The following examples illustrate the invention without limiting it.

EXAMPLES

Example 1: Composition Based on Odor-Masked Tertiary Amine

In order to characterize a perfuming composition which may serve as masking agent, i.e. which makes it possible to improve, reduce or eliminate the odor of a tertiary amine, an olfactory test procedure and an examination of stability were developed.

Operating Conditions:

In order to carry out this olfactory test, an amount of 1 ml of composition (amine and odor-masking agent) is placed in a container. The container containing the composition is then placed in a 10 liter dessicator.

The dessicator is left in the open air at room temperature (25° C.). After total evaporation (approximately 30 minutes), a panel composed of 10 people inhale the composition in order to grade the odor (hedonic test).

When the panelists have smelt the compositions, they note the odor of the composition. Depending on their preference, they allocate one or more crosses to each of the compositions to be tested. The number of crosses given by the panelists ranges from 1 (most unpleasant product) to 3 (most pleasant product).

For the examination of stability, the compositions are stored at room temperature (25° C.) for a duration ranging from 1 month to more than 1 year.

Preparation of Test Specimens:

Each composition is prepared with a tertiary amine, dimethylethylamine (DMEA) provided by Arkema. The DMEA has a purity of greater than or equal to 99%.

A reference sample is produced with pure DMEA and is named A1. Three samples comprising 99.92% by weight relative to the total weight of the DMEA sample and 0.08% by weight relative to the total weight of the sample of a perfuming composition are also prepared. The samples are named: $A_2$, $A_3$ and $A_4$.

The nature of the masking agent of each of the samples $A_2$, $A_3$ and $A_4$ is given below, in which the percentages are expressed by weight relative to the total weight of the masking agent:

Sample $A_2$ (Comparative Test): Odor-Masking Agent: OMA-A2
  30% to 70% esters (2-tert-butylcyclohexyl acetate, 3-methylbutyl butyrate, 2-propylene-3-cyclohexyl propanoate, 4-undecanolide, isopentyl acetate),
  15% to 35% ketones (5-methyl-3-heptanone, 1-cyclooct-3-enylethanone),
  15% to 35% ethers (1,3,4,6,7,8-hexahydro-4,6,6,7,8,8-hexamethylindeno[5,6-c]pyran),
in which the sum of the constituents represents 100% by weight of the masking agent.

Sample $A_3$ (Comparative Test): Odor-Masking Agent: OMA-A3
  30% to 50% esters (3a,4,5,6,7,7a-hexahydro-4,7-methano-1-inden-5(6)-yl acetate, methyl benzoate, 2-acetyl-1,2,3,4,5,6,7,8-octahydro-2,3,8,8-tetramethylnaphthalene),
  30% to 50% ketones and aldehydes (3-methyl-4-(2,6,6-trimethyl-2-cyclohexen-1-yl)-3-buten-2-one, 2-methylundecanal, heptan-2-one, 1-(2,6,6-trimethylcyclohex-2-en-1-yl)pent-1-en-3-one, 3-phenyl-2-propenal, 3-phenylbutanal),
  1% to 10% alcohols (3,7-dimethyloctan-3-ol, 3,7-dimethyl-2,6-octadien-1-ol),
  1% to 10% ethers (2-methoxynaphthalene),
in which the sum of the constituents represents 100% by weight of the masking agent.

Sample $A_4$ (According to the Invention): Odor-Masking Agent: OMA-B1
  10% to 98% ethers (phenoxybenzene, 2-methoxynaphthalene),
  from 10% to 98% terpenes/terpenoids (limonene, eucalyptol),
  from 1% to 10% oximes (5-methyl-3-heptanone oxime),
  from 0.1% to 1% additives, mainly esters (triethyl citrate, isopropyl tetradecanoate),
in which the sum of the constituents represents 100% by weight of the masking agent.

Results:
The results of example 1 are reproduced in the following table 1:

TABLE 1

| Sample to be tested | Odor | Storage stability (at room temperature) |
|---|---|---|
| $A_1$ | + | Colorless, stable (more than one year) |
| $A_2$ | ++ | Yellow (after 1 month), unstable |
| $A_3$ | ++ | Yellow (after 1 month), unstable |
| $A_4$ | ++++ | Colorless, stable (after 3 months) |

In example 1 of the present invention, the perception of the odor of the composition according to the invention $A_4$ is considerably more pleasant than in samples $A_1$, $A_2$ and $A_3$.

Moreover, sample $A_4$ remains colorless and stable after 3 months of storage at room temperature, whereas samples $A_2$ and $A_3$, which are unstable, become yellow in color after 1 month of storage at room temperature.

Example 2: Composition Based on Odor-Masked Tertiary Amine According to the Invention The operating procedure of example 1 is reproduced in order to prepare two new samples $A_5$ and $A_6$, which differ from sample $A_4$ in terms of the content of masking agent, as indicated below:

Sample $A_4$ (According to the Invention):
  DMEA: 99.92% by weight relative to the total weight of the sample, and
  odor-masking agent OMA-B1: 0.08% by weight relative to the total weight of the sample.

Sample $A_5$ (According to the Invention):
  DMEA: 99.86% by weight relative to the total weight of the sample, and
  odor-masking agent OMA-B1: 0.14% by weight relative to the total weight of the sample.

Sample $A_6$ (According to the Invention):
  DMEA: 99.75% by weight relative to the total weight of the sample, and
  odor-masking agent OMA-B1: 0.25% by weight relative to the total weight of the sample.

Results:
The results of example 2 are reproduced in the following table 2:

TABLE 2

| Sample to be tested | Odor | Storage stability (at room temperature) |
|---|---|---|
| $A_1$ | + | Colorless, stable (more than one year) |
| $A_4$ | ++++ | Colorless, stable (after 3 months) |
| $A_5$ | ++++ | Colorless, stable (after 3 months) |
| $A_6$ | ++ | Colorless, stable (after 3 months) |

The results from table 2 show that the perception of the odor of the compositions according to the invention $A_4$, $A_5$ and $A_6$ is considerably more pleasant than in sample $A_1$, and that the increase in the dose of odor-masking agent leads to a slight decrease in the pleasant olfactory perception of the composition.

Moreover, samples $A_4$, $A_5$ and $A_6$ remain colorless and stable after 3 months of storage at room temperature, irrespective of the amount of masking agent incorporated into the DMEA.

The invention claimed is:
1. A composition, comprising:
  (a) at least 90% by weight of at least one primary, secondary or tertiary amine represented by formula (I), relative to the total weight of the composition,

wherein
  $R_1$, $R_2$ and $R_3$, which may be identical or different, are selected independently of one another from a hydrogen atom, a linear or branched alkyl radical comprising from 1 to 12 carbon atoms, or a cycloalkyl radical comprising from 3 to 12 carbon atoms, or two of the substituents selected from $R_1$, $R_2$ and $R_3$, together and with the nitrogen atom to which they are bonded, form a ring structure comprising from 2 to 12 carbon atoms, and optionally comprising one or more heteroatoms selected from oxygen, nitrogen, sulfur or phosphorus, and being optionally substituted with one or more functional groups selected from hydroxyl, alkoxy, alkylcarbonyl, alkoxycarbonyl, benzyl, fluorine, chlorine, bromine, iodine, sulfur, phosphorus or nitrogen, and at least one of is $R_1$, $R_2$ and $R_3$ is not hydrogen; and
(b) an odor-masking agent,
wherein
the composition comprises at most 10% by weight of the odor-masking agent, relative to the total weight of the composition; and
the odor-masking agent comprises at least one ether represented by formula (b1):

$$R_4\text{—O—}R_5 \quad (b1)$$

wherein
$R_4$ and $R_5$, which may be identical or different, are selected independently of one another from a linear or branched alkyl radical comprising from 1 to 12 carbon atoms, a cycloalkyl radical comprising from 3 to 12 carbon atoms, an alkenyl radical comprising from 2 to 12 carbon atoms, a cycloalkenyl radical comprising from 3 to 12 carbon atoms, a phenyl radical or a benzyl radical, or $R_4$ and $R_5$, together and with the oxygen atom to which they are bonded, form a ring structure comprising from 3 to 20 atoms, optionally comprising one or more heteroatoms selected from oxygen, nitrogen, sulfur and phosphorus, wherein the ring structure is optionally substituted with one or more groups selected from hydroxyl, alkoxy, alkylcarbonyl, alkoxycarbonyl, phenyl, benzyl, fluorine, chlorine, bromine, iodine, sulfur, phosphorus or nitrogen.

2. The composition of claim 1, wherein the odor-masking agent further comprises:
(b2) at least one terpene and/or one terpenoid.

3. The composition of claim 1, wherein the odor-masking agent further comprises:
at least one oxime represented by formula (b3):

(b3)

wherein
$R_6$ is selected from a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, a phenyl radical or a benzyl radical, and $R_7$ is selected from a hydrogen atom, a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, a phenyl radical or a benzyl radical, or $R_6$ and $R_7$, together and with the carbon atom to which they are bonded, form a ring structure comprising from 3 to 20 atoms, and optionally comprising one or more heteroatoms selected from oxygen, nitrogen, sulfur or phosphorus, wherein the ring structure is optionally substituted with one or more groups selected from hydroxyl, alkoxy, phenyl, benzyl, fluorine, chlorine, bromine, iodine, sulfur, phosphorus or nitrogen.

4. The composition of claim 1, wherein the amine is a primary amine.

5. The composition of claim 1, wherein the amine is selected from the group consisting of propan-1-amine, propan-2-amine, cyclopentanamine, 2-methylpropan-2-amine, phenylmethanamine, 2-aminopentane, 3-aminopentane, 1,2-dimethylpropylamine, hexylamine, 1,3-dimethylbutylamine, n-heptylamine, n-octylamine, 2-aminooctane, 3,3,5-trimethylcyclohexylamine, ethylamine (MEA), isopropylamine, sec-butylamine, 3-ethoxypropylamine, 3-(2-methoxyethoxy)propylamine, 3-butoxypropylamine, 3-(2-ethylhexyloxy)propylamine, 3-isopropoxypropylamine, 3-methoxypropylamine, and mixtures thereof.

6. The composition of claim 1, wherein the amine is selected from the group consisting of N-methylethanamine, N-ethylethanamine, N-methylpentan-3-amine, N-3-dimethylbutan-2-amine, di(sec-butyl)amine, diamylamine, isopropylbenzylamine, dihexylamine, diethylamine, diisopropylamine, N-isopropylmethylamine, N-butylmethylamine, N-(sec-butyl)methylamine, N-isobutylmethylamine, N-(tert-butyl)methylamine, N-methylpentylamine, N-hexylmethylamine, N-methylcyclohexylamine, N-heptylmethylamine, N-octylmethylamine, N-ethylmethylamine, N-ethylpropylamine, N-ethylisopropylamine, N-butylethylamine, N-(sec-butyl)ethylamine, N-ethylcyclohexylamine, N-ethylbenzylamine, and mixtures thereof.

7. The composition of claim 1, wherein the amine is selected from the group consisting of trimethylamine, N-methylaziridine, dimethylethylamine (DMEA), N-methylazetidine, N-ethylaziridine, diethylmethylamine (DEMA), dimethylisopropylamine (DMIPA), dimethyl(n-propyl)amine (DMPA), N-(n-propyl)aziridine, N-isopropylaziridine, N-ethylazetidine, N-methylpyrrolidine, N,N,N',N-tetramethyldiaminomethane, triethylamine (TEA), methylethyl(n-propyl)amine, methylethylisopropylamine, dimethyl(n-butyl)amine, dimethyl(sec-butyl)amine, dimethylisobutylamine, dimethyl(tert-butyl)amine, N-ethylpyrrolidine, N-methylpiperidine, hexamethylenetetramine, dimethylpiperazine, N,N,N',N'-tetramethyldiaminoethane, dimethylpentylamines, methylethylbutylamines, diethylamines, dipropylmethylamines, N-propylpyrrolidines, N-ethylpiperidine, dimethylhexylamines, methylethylpentylamines, diethylbutylamines, dipropylethylamines, N-butylpyrrolidines, N-propylpiperidines, diethylpiperazine, dimethylheptylamines, methylethylhexylamines, diethylpentylamines, tripropylamines, N-pentylpyrrolidines, N-butylpiperidines, dimethyloctylamines, methylethylheptylamines, diethylhexylamines, ethylpropylpentylamines, dipropylbutylamines, N-pentylpiperidines, ethyldiisopropylamine, and mixtures thereof.

8. The composition of claim 1, wherein the amine is selected from the group consisting of DMEA, DMIPA, DEMA, DMPA, TEA, and mixtures thereof.

9. The composition of claim 1, wherein the amine comprises DMEA.

10. The composition of claim 1, wherein the ether represented formula (b1) is selected from the group consisting of phenoxybenzene, diphenyl ether, methoxynaphthalenes, 1-methoxy-4-methyl-(4-methylanisole), 2-(2,4-dimethylcyclohex-3-en-1-yl)-5-methyl-(1-methylpropyl)-1,3-dioxane, methoxymethane, methoxyethane, ethoxyethane, 2-ethoxypropane, oxacyclopropane, oxacyclopentane, oxacyclohexane, 1,4-dioxacyclohexane, dimethoxymethane, diisopropyl ether, tetrahydrofuran, 1,4-dioxane, pyrans, dihydropyrans, phenylpyrans, dihydrophenylpyrans, pyrans and dihydropyrans substituted by at least one of a phenyl or an alkyl group, and mixtures thereof.

11. The composition of claim 1, wherein the odor-masking agent further comprises:
   (b2) at least one terpene/terpenoid selected from the group consisting of terpinenes, myrcene, limonene, terpinolene, pinenes, sabinene, camphene, ocimene, eucalyptol, citral, menthol, camphor, menthone, terpineol, isoborneol, nerol, citronellal, citronellol, linalool, geraniol, myrcenol, essential oils based on terpenes and/or terpenoids, and mixtures thereof.

12. The composition of claim 1, wherein the odor-masking agent further comprises
   (b3) at least one oxime selected from the group consisting of cinnamaldehyde oxime, 2-methylbutanal oxime, 3-methylbutanal oxime, methyl ethyl ketoxime, 3-heptanone oxime, 5-methyl-3-heptanone oxime, glyoxime, dimethylglyoxime, diaminoglyoxime, pralidoxime, obidoxime, perillartine, asoxime chloride, salicylaldoxime, and mixtures thereof.

13. The composition of claim 1, wherein the odor-masking agent further comprises:
   (b2) at least one terpene/terpenoid, and
   (b3) at least one oxime.

14. The composition of claim 1, wherein the amine is a secondary amine.

15. The composition of claim 1, wherein the amine is a tertiary amine.

16. The composition of claim 1, comprising at least 95% by weight of (a) and at most 5% by weight of (b), relative to the total weight of the composition.

17. The composition of claim 1, comprising at least 99% by weight of (a) and at most 1% by weight of (b), relative to the total weight of the composition.

18. The composition of claim 1, comprising at least 99.5% by weight of (a) and at most 0.5% by weight of (b), relative to the total weight of the composition.

19. A method of preparing the composition of claim 1, comprising combining (a) and (b).

20. A method of manufacturing a polymer, comprising manufacturing a polymer in the presence of the composition of claim 1.

21. A method of manufacturing a foundry mold, comprising manufacturing a foundry mold in the presence of the composition of claim 1.

22. A foundry mold obtained by crosslinking a binder mixed with an aggregate in the presence of the composition of claim 1.

23. A method of masking the odor of a secondary or tertiary amine, comprising combining at least one secondary or tertiary amine with an effective amount of an odor-masking agent comprising:
   at least one ether represented by formula (b1):

$$R_4\text{—}O\text{—}R_5 \tag{b1}$$

wherein
   $R_4$ and $R_5$, which may be identical or different, are selected independently of one another from a linear or branched alkyl radical comprising from 1 to 12 carbon atoms, a cycloalkyl radical comprising from 3 to 12 carbon atoms, an alkenyl radical comprising from 2 to 12 carbon atoms, a cycloalkenyl radical comprising from 3 to 12 carbon atoms, a phenyl radical or a benzyl radical, or
   $R_4$ and $R_5$, together and with the oxygen atom to which they are bonded, form a ring structure comprising from 3 to 20 atoms, optionally comprising one or more heteroatoms selected from oxygen, nitrogen, sulfur and phosphorus, wherein the ring structure is optionally substituted with one or more groups selected from hydroxyl, alkoxy, alkylcarbonyl, alkoxycarbonyl, phenyl, benzyl, fluorine, chlorine, bromine, iodine, sulfur, phosphorus or nitrogen, and
   at least one oxime represented by formula (b3):

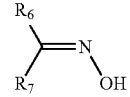

(b3)

wherein
   $R_6$ is selected from a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, a phenyl radical or a benzyl radical, and $R_7$ is selected from a hydrogen atom, a linear or branched alkyl radical comprising from 1 to 24 carbon atoms, a cycloalkyl radical comprising from 3 to 24 carbon atoms, an alkenyl radical comprising from 2 to 24 carbon atoms, a cycloalkenyl radical comprising from 3 to 24 carbon atoms, a phenyl radical or a benzyl radical, or
   $R_6$ and $R_7$, together and with the carbon atom to which they are bonded, form a ring structure comprising from 3 to 20 atoms, and optionally comprising one or more heteroatoms selected from oxygen, nitrogen, sulfur or phosphorus, wherein the ring structure is optionally substituted with one or more groups selected from hydroxyl, alkoxy, phenyl, benzyl, fluorine, chlorine, bromine, iodine, sulfur, phosphorus or nitrogen.

* * * * *